United States Patent
Kuwayama et al.

(10) Patent No.: US 6,677,464 B2
(45) Date of Patent: Jan. 13, 2004

(54) PROCESS FOR PREPARATION OF 7-OXABICYCLO[2.2.1]HEPT-5-ENE-2-CARBOXYLIC ACID DERIVATIVES

(75) Inventors: Tomoya Kuwayama, Okayama (JP); Katsuji Ujita, Okayama (JP); Kazuya Shimizu, Okayama (JP); Shiro Terashima, Tokyo (JP)

(73) Assignees: Kuraray Co., Ltd., Okayama (JP); Sagami Chemical Research Center, Kanagawa (JP)

(*) Notice: Subject to any disclaimer, the term of this patent is extended or adjusted under 35 U.S.C. 154(b) by 0 days.

(21) Appl. No.: 10/363,857

(22) PCT Filed: Sep. 14, 2001

(86) PCT No.: PCT/JP01/07978

§ 371 (c)(1), (2), (4) Date: Mar. 14, 2003

(87) PCT Pub. No.: WO02/22619

PCT Pub. Date: Mar. 21, 2002

(65) Prior Publication Data

US 2003/0187282 A1 Oct. 2, 2003

(30) Foreign Application Priority Data

Sep. 18, 2000 (JP) ........................ 2000-282140

(51) Int. Cl.[7] .......................... C07D 493/08
(52) U.S. Cl. ............................. 549/463
(58) Field of Search ........................ 549/463

(56) References Cited

PUBLICATIONS

J.A. Moore et al.: "Catalyzed addition of furan with acrylic monomers" J. Organic Chemistry, vol. 48, No. 7, pp. 1105–1106, 1983.

Carbohydrate Research, vol. 58, pp. 240–244, 1977.
Bull. Chem. Soc. Jpn., vol. 55, pp. 496–499, 1982.
J. Mol. Catal. A: Chem., vol. 123, pp. 43–47, 1997.
Heterocycl. Chem., vol. 9, pp. 561–568, 1972.
J.A. Moore et al.: "Catalyzed additiona of furan with acrylic monomers", J. Organic Chemistry, vol. 48, No. 7, pp. 1105–1106, 1993.

*Primary Examiner*—Patricia L. Morris

(57) ABSTRACT

The present invention provides a method of industrially advantageously producing 7-oxabicyclo[2.2.1]hept-5-ene-2-carboxylic acid derivatives under mild conditions in a high yield. The present invention relates to a production method of a 7-oxabicyclo[2.2.1]hept-5-ene-2-carboxylic acid derivative of the formula (III) or the formula (IV), which comprises reacting an α,β-unsaturated carboxylic acid of the formula (I) with a furan derivative of the formula (II) in the presence of a Lewis acid:

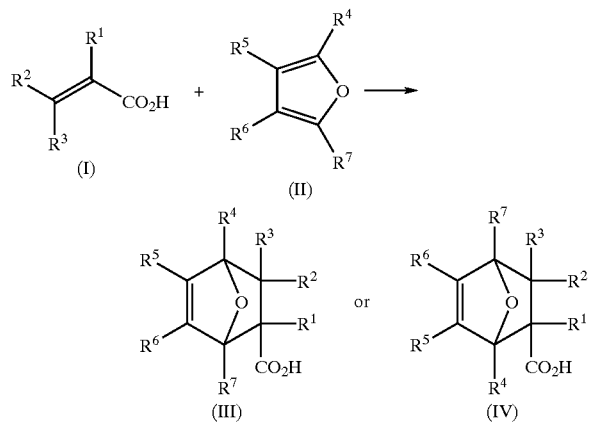

wherein each symbol is as defined in the specification.

4 Claims, No Drawings

PROCESS FOR PREPARATION OF 7-OXABICYCLO[2.2.1]HEPT-5-ENE-2-CARBOXYLIC ACID DERIVATIVES

TECHNICAL FIELD

The present invention relates to a production method of 7-oxabicyclo[2.2.1]hept-5-ene-2-carboxylic acid derivatives. An endo form of a 7-oxabicyclo[2.2.1]hept-5-ene-2-carboxylic acid derivative obtained by the method of the present invention is useful as a starting material for the synthesis of medicine, agricultural chemical and the like. For example, an endo form of 7-oxabicyclo[2.2.1]hept-5-ene-2-carboxylic acid is a useful compound as a synthetic intermediate for Cyclophellitol, an anti-HIV drug [see Tetrahedron Letters, vol. 37, p. 3043 (1996)], as a synthetic intermediate for Validamycin A, an antibiotic [see Carbohydrate Research, vol. 58, p. 240 (1977)], and as a synthetic intermediate for GS4104, an anti-influenza drug [see Journal of the American Chemical Society (J. Am. Chem. Soc.), vol. 119, p. 681 (1997); The Journal of organic Chemistry (J. Org. Chem.), vol. 63, p. 4545 (1998); specification of WO 01/47906].

BACKGROUND ART

A number of physiologically active substances derived from an oxanorbornene skeleton have been found in recent years. Known production methods of 7-oxabicyclo[2.2.1]hept-5-ene-2-carboxylic acid derivative useful as a synthetic intermediate for these compounds include (1) a method comprising a reaction of acrylic acid with furan in the presence of hydroquinone [see Carbohydrate Research, vol. 58, p. 240 (1977)], (2) a method comprising a reaction of an acrylic acid derivative with furan in the presence of tetrakis(acetonitrile)copper(I) tetrafluoroborate and hydroquinone [see The Journal of organic Chemistry (J. Org. Chem.), vol. 48, p. 1105 (1983)], (3) a method comprising a reaction of an acrylic acid derivative with furan under high pressure conditions of 1 to 2 MPa (10 to 20 kbar) [see The Bulletin of the Chemical Society of Japan (Bull. Chem. Soc. Japan), vol. 55, p. 4969 (1982)], (4) a method comprising a reaction of an acrylic acid ester with furan in the presence of zinc chloride, zinc iodide or titanium chloride [see Journal of Molecular Catalysis A: Chemical (J. Mol. Catal. A: Chem.), vol. 123, p. 43 (1997)], and then hydrolysis of the ester moiety of the obtained compound [see Journal of Heterocyclic Chemistry (J. Heterocycl. Chem.), vol. 9, p. 561 (1972)] and the like.

The reaction to form the 7-oxabicyclo[2.2.1]hept-5-ene skeleton by Diels-Alder reaction of dienophile such as an acrylic acid derivative with furan has been considered to resist promotion of the reaction by heating, because cycloaddition products are unstable to heat. In the above-mentioned methods (1) and (2), therefore, the reaction is carried out for a long time in the presence of hydroquinone as a polymerization inhibitor, and in the above-mentioned method (3), the reaction is carried out under high pressure conditions.

However, the method of the above-mentioned (1) is problematic in that the reaction time is extremely long (75 days) and the yield is as low as 33%. In addition, the method of the above-mentioned (2) is also problematic in that the reaction time is long (9 days) and the yield is as low as 48%, and the method of the above-mentioned (3) essentially requires a pressure reactor, which increases costs of facilities. Furthermore, the method of the above-mentioned (4) requires a Diels-Alder reaction step of an acrylic acid ester with furan and a hydrolysis step of the ester moiety, thus problematically having many steps. Therefore, it is difficult to say that these methods are industrially advantageous production methods of 7-oxabicyclo[2.2.1]hept-5-ene-2-carboxylic acid derivatives.

DISCLOSURE OF THE INVENTION

It is therefore an object of the present invention to provide a production method capable of industrially advantageously producing a 7-oxabicyclo[2.2.1]hept-5-ene-2-carboxylic acid derivative under mild conditions in a high yield. In other words, in the method of producing a 7-oxabicyclo[2.2.1]hept-5-ene-2-carboxylic acid derivative directly from an acrylic acid derivative and a furan derivative, the present invention aims at providing a method for producing the objective compound in a shorter reaction time in a high yield under mild conditions (without the need for heating at a high temperature or pressurizing).

The present invention provides a production method of a 7-oxabicyclo[2.2.1]hept-5-ene-2-carboxylic acid derivative of the formula (III)

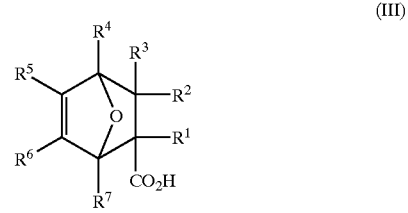

wherein $R^1$, $R^2$ and $R^3$ are each independently a hydrogen atom, a halogen atom, a formyl group, a cyano group, a carboxyl group, an alkoxycarbonyl group, an acyl group, an acyloxy group, an organic sulfinyl group, an organic sulfonyl group or an alkyl group optionally having substituents, or $R^1$ and $R^2$ may form a ring together with the carbon atoms they are bonded to, and $R^4$, $R^5$, $R^6$ and $R^7$ are independently a hydrogen atom, an alkoxyl group, an alkylthio group or an alkyl group optionally having substituents, or $R^4$ and $R^5$, and $R^5$ and $R^6$ may form a ring together with the carbon atoms they are bonded to, or the formula (IV)

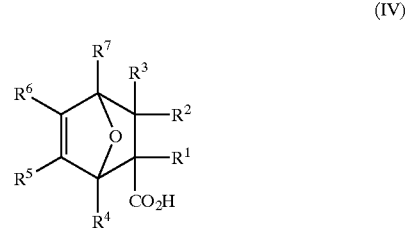

wherein $R^1$, $R^2$, $R^3$, $R^4$, $R^5$, $R^6$ and $R^7$ are as defined above 5 [hereinafter to be abbreviated as 7-oxabicyclo[2.2.1]hept-5-ene-2-carboxylic acid derivative (III) and 7-oxabicyclo[2.2.1]hept-5-ene-2-carboxylic acid derivative (IV), respectively], which comprises:

reacting an α,β-unsaturated carboxylic acid of the formula (I)

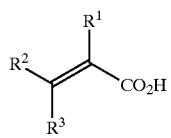
(I)

wherein $R^1$, $R^2$ and $R^3$ are as defined above [hereinafter to be abbreviated as α,β-unsaturated carboxylic acid (I)], with a furan derivative of the formula (II)

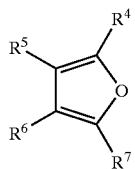
(II)

wherein $R^4$, $R^5$, $R^6$ and $R^7$ are as defined above [hereinafter to be abbreviated as furan derivative (II)], in the presence of a Lewis acid.

The present invention provides a production method of a 7-oxabicyclo[2.2.1]hept-5-ene-2-carboxylic acid derivative of the formula (III-1)

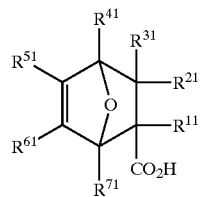
(III-1)

wherein
$R^{11}$, $R^{21}$ and $R^{31}$ are each independently a hydrogen atom, a halogen atom or a carboxyl group, or $R^{11}$ and $R^{21}$ may form a ring together with the carbon atoms they are bonded to, and $R^{41}$, $R^{51}$, $R^{61}$ and $R^{71}$ are each independently a hydrogen atom or an alkyl group optionally having substituents, or $R^{41}$ and $R^{51}$, and $R^{51}$ and $R^{61}$ may form a ring together with the carbon atoms they are bonded to, or the formula (IV-1)

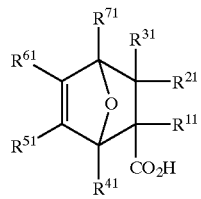
(IV-1)

wherein $R^{11}$, $R^{21}$, $R^{31}$, $R^{41}$, $R^{51}$, $R^{61}$ and $R^{71}$ are as defined above [hereinafter to be abbreviated as 7-oxabicyclo[2.2.1] hept-5-ene-2-carboxylic acid derivative (III-1) and 7-oxabicyclo[2.2.1]hept-5-ene-2-carboxylic acid derivative (IV-1), respectively], which comprises:

reacting an α,β-unsaturated carboxylic acid of the formula (I-,1)

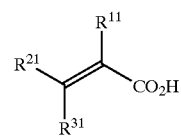
(I-1)

wherein $R^{11}$, $R^{21}$ and $R^{31}$ are as defined above [hereinafter to be abbreviated as α,β-unsaturated carboxylic acid (I-1)], with a furan derivative of the formula (II-1)

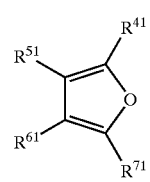
(II-1)

wherein $R^{41}$, $R^{51}$, $R^{61}$ and $R^{71}$ are as defined above [hereinafter to be abbreviated as furan derivative (II-1)], in the presence of a Lewis acid.

In a preferable embodiment, a boron compound having Lewis acidity is used as a Lewis acid. In a preferable embodiment, a Lewis acid selected from the group consisting of a borane-tetrahydrofuran complex, a borane-dimethyl sulfide complex, a boron trifluoride-diethyl ether complex, triacetoxyborane and lo tripropionyloxyborane can be also used as a Lewis acid. Alternatively, in another embodiment, a Lewis acid selected from the group consisting of anhydrous aluminum chloride, anhydrous ferric chloride and zinc chloride can be used as a Lewis acid.

The halogen atom represented by $R^1$, $R^2$, $R^3$, $R^{11}$, $R^{21}$ and $R^{31}$ in the above-mentioned formulas is exemplified by a fluorine atom, a chlorine atom, a bromine atom, an iodine atom and the like.

The alkyl group represented by $R^1$, $R^2$, $R^3$, $R^4$, $R^5$, $R^6$, $R^7$, $R^{41}$, $R^{51}$, $R^{61}$ and R71 is exemplified by a straight chain or branched chain alkyl group preferably having 1 to 10 carbon atoms, more preferably 1 to 6 carbon atoms, such as a methyl group, an ethyl group, a propyl group, an isopropyl group, a butyl group, an isobutyl group, a tert-butyl group and a hexyl group. These alkyl groups may have substituents and examples of the substituent include a halogen atom such as a fluorine atom, a chlorine atom, a bromine atom and an iodine atom; an alkoxyl group preferably having 1 to 6 carbon atoms such as a methoxy group, an ethoxy group, a propoxy group and a butoxy group; a tri-substituted silyloxy group such as a tert-butyldimethylsilyloxy group and a tert-butyldiphenylsilyloxy group; and the like. As used herein, the tri-substituted silyloxy group means a silyloxy group substituted by 3 substituents selected from an alkyl group (preferably an alkyl group having 1 to 6 carbon atoms) and a phenyl group.

The alkoxyl group represented by $R^4$, $R^5$, $R^6$ and $R^7$ is exemplified by a straight chain or branched chain alkoxyl group preferably having 1 to 10 carbon atoms, more preferably 1 to 6 carbon atoms, such as a methoxy group, an ethoxy group, a propoxy group and a butoxy group. The alkylthio group represented by $R^4$, $R^5$, $R^6$ and $R^7$ is exemplified by a straight chain or branched chain alkylthio group preferably having 1 to 10 carbon atoms, more preferably 1 to 6 carbon atoms, such as a methylthio group, an ethylthio group, a propylthio group and a butylthio group.

The alkoxycarbonyl group represented by $R^1$, $R^2$ and $R^3$ is exemplified by an alkoxycarbonyl group wherein the alkoxyl moiety preferably has 1 to 10 carbon atoms, more preferably 1 to 6 carbon atoms, such as a methoxycarbonyl group, an ethoxycarbonyl group and a tert-butoxycarbonyl group. The acyl group represented by $R^1$, $R^2$ and $R^3$ is exemplified by an alkanoyl group preferably having 2 to 10 carbon atoms, more preferably 2 to 6 carbon atoms, such as an acetyl group, a propanoyl group, a butanoyl group and a pivaloyl group; and an aroyl group such as a benzoyl group. The acyloxy group represented by $R^1$, $R^2$ and $R^3$ is exemplified by an alkanoyloxy group preferably having 2 to 10 carbon atoms, more preferably 2 to 6 carbon atoms, such as an acetoxy group, a propanoyloxy group, a butanoyloxy group and a pivaloyloxy group; and an aroyloxy group such as a benzoyloxy group.

The organic sulfinyl group represented by $R^1$, $R^2$ and $R^3$ is a sulfinyl group to which an organic group is bonded, and examples thereof include an alkyl sulfinyl group optionally having substituents, an arylsulfinyl group optionally having substituents and the like. The alkyl moiety of the alkyl sulfinyl group is an alkyl group preferably having 1 to 6 carbon atoms. The aryl moiety of the arylsulfinyl group is exemplified by a phenyl group. The substituent that the alkyl sulfinyl group may have is exemplified by an alkoxyl group (preferably an alkoxyl group having 1 to 6 carbon atoms), a halogen atom, a cyano group, a nitro group and the like. The substituent that the arylsulfinyl group may have on the aromatic ring is exemplified by an alkyl group (preferably an alkyl group having 1 to 6 carbon atoms), an alkoxyl group (preferably an alkoxyl group having 1 to 6 carbon atoms), a halogen atom, a cyano group, a nitro group and the like. The organic sulfinyl group represented by $R^1$, $R^2$ and $R^3$ is exemplified by a methanesulfinyl group, an ethanesulfinyl group, a benzenesulfinyl group, a p-toluenesulfinyl group and the like.

The organic sulfonyl group represented by $R^1$, $R^2$ and $R^3$ is a sulfonyl group to which an organic group is bonded, and examples thereof include an alkylsulfonyl group optionally having substituents, an arylsulfonyl group optionally having substituents, a halosulfonyl group, an alkoxysulfonyl group optionally having substituents and the like. The alkyl moiety of the alkylsulfonyl group is an alkyl group preferably having 1 to 6 carbon atoms, and the alkoxyl moiety of the alkoxysulfonyl group is an alkoxyl group preferably having 1 to 6 carbon atoms. The aryl moiety of the arylsulfonyl group is exemplified by a phenyl group. The substituent that the alkylsulfonyl group and the alkoxysulfonyl group may have is exemplified by an alkoxyl group (preferably an alkoxyl group having 1 to 6 carbon atoms), a halogen atom, a cyano group, a nitro group and the like. The substituent that the arylsulfonyl group may have on the aromatic ring is exemplified by an alkyl group (preferably an alkyl group having 1 to 6 carbon atoms), an alkoxyl group (preferably an alkoxyl group having 1 to 6 carbon atoms), a halogen atom, a cyano group, a nitro group and the like. The halogen atom that the halosulfonyl group has is exemplified by a chlorine atom, a bromine atom and the like. The organic sulfonyl group represented by $R^1$, $R^2$ and $R^3$ is exemplified by a methanesulfonyl group, an ethanesulfonyl group, a benzenesulfonyl group, a p-toluenesulfonyl group, a chlorosulfonyl group, a bromosulfonyl group, a methoxysulfonyl group, an ethoxysulfonyl group, a trifluoromethoxysulfonyl group and the like.

The ring that may be formed by $R^1$ and $R^2$, $R^4$ and $R^5$, $R^{11}$ and $R^{21}$ or $R^{41}$ and $R^{51}$ together with the carbon atoms they are bonded to is preferably a 4 to 7-membered ring. In the case of the formula (I), (II), (I-1) or (II-1), a cyclobutene ring, a cyclopentene ring, a cyclohexene ring, a cyclohep-tene ring and the like are exemplified; and in the case of the formula (III), (IV), (III-1) or (IV-1), a cyclobutane ring, a cyclopentane ring, a cyclohexane ring, a cycloheptane ring and the like are exemplified. The ring that may be formed by $R^5$ and $R^6$ or $R^{51}$ and $R^{61}$ together with the carbon atoms they are bonded to is preferably a 4 to 7-membered ring. In the case of the formula (II) or (II-1), a cyclobutane ring, a cyclopentane ring, a cyclohexane ring, a cycloheptane ring and the like are exemplified; and in the case of the formula (III), (IV), (III-1) or (IV-1), a cyclobutene ring, a cyclopentene ring, a cyclohexene ring, a cycloheptene ring and the like are exemplified. These rings may have substituents and examples of the substituent include an alkyl group (preferably an alkyl group having 1 to 6 carbon atoms), an alkoxyl group (preferably an alkoxyl group having 1 to 6 carbon atoms), an alkoxycarbonyl group (preferably an alkoxycarbonyl group wherein the alkoxyl moiety has 1 to 6 carbon atoms), an acyl group (preferably an alkanoyl group having 2 to 6 carbon atoms), a halogen atom, a cyano group, a nitro group and the like.

The $\alpha,\beta$-unsaturated carboxylic acid (I-1) is encompassed in $\alpha,\beta$-unsaturated carboxylic acid (I), and the furan derivative (II-1) is encompassed in furan derivative (II). The 7-oxabicyclo[2.2.1]hept-5-ene-2-carboxylic acid derivative (III-1) is encompassed in 7-oxabicyclo[2.2.1]hept-5-ene-2-carboxylic acid derivative (III), and 7-oxabicyclo[2.2.1]hept-5-ene-2-carboxylic acid derivative (IV-1) is encompassed in 7-oxabicyclo[2.2.1]hept-5-ene-2-carboxylic acid derivative (IV).

The reaction of $\alpha,\beta$-unsaturated carboxylic acid (I) with furan derivative (II) can be carried out in the presence or absence of a solvent. The solvent to be used is free of any particular limitation as long as it does not adversely affect the reaction. Examples of the solvent include an aliphatic hydrocarbon such as pentane, hexane, heptane, octane and petroleum ether; an aromatic hydrocarbon such as benzene, toluene, xylene, ethylbenzene and cumene; an ether such as diethyl ether, tetrahydrofuran, diisopropyl ether, dimethoxyethane, dibutyl ether and 1,4-dioxane; a halogenated hydrocarbon such as dichloromethane, chloroform, carbon tetrachloride, dichloroethane, trichloroethane, chlorobenzene and dichlorobenzene; or a mixed solvent thereof; and the like. The amount of the solvent to be used is free of any particular limitation, but it is generally preferably a 0.1 to 100-fold weight relative to $\alpha,\beta$-unsaturated carboxylic acid (I).

Examples of the Lewis acid include anhydrous aluminum chloride, aluminum bromide, diethylaluminum chloride, gallium chloride, gallium bromide, gallium iodide, anhydrous ferric chloride, anhydrous ferric bromide, zinc chloride, zinc bromide, zinc iodide, titanium chloride, titanium iodide, anhydrous stannous chloride, stannous bromide, anhydrous stannic chloride, a borane-tetrahydrofuran complex ($BH_3 \cdot THF$), a borane-dimethyl sulfide complex ($BH_3 \cdot (CH_3)_2S$), boron trichloride, boron tribromide, a boron trifluoride-diethyl ether complex ($BF_3 \cdot (C_2H_5)_2O$), a chloroborane-diethyl ether complex ($BH_2Cl \cdot (C_2H_5)_2O$), a chloroborane-dimethyl sulfide complex ($BH_2Cl \cdot (CH_3)_2S$), a dichloroborane-dimethyl sulfide complex ($BHCl_2 \cdot (CH_3)_2S$), a bromoborane-dimethyl sulfide complex ($BH_2Br \cdot (CH_3)_2S$), a dibromoborane-dimethyl sulfide complex ($BHBr_2 \cdot (CH_3)_2S$); an acyloxyborane compound such as tris(2,4,6-trimethylbenzoyloxy)borane, bis(chloroacetoxy)borane, triacetoxyborane, tri(fluoroacetoxy)borane, tripropionyloxyborane, triacryloyloxyborane, trimethacryloyloxyborane; a dioxoborane compound such as $\alpha$-[2,6-bis(isopropoxy)benzoyl]oxy-5-oxo-1,3,2- dioxaborane; an oxazaborolidine compound such as 4-isopropyl-3-paratoluenesulfonyl-1,3,2-oxazaborolidin-5-one and 4-t-butyl-3-paratoluenesulfonyl-1,3,2-oxazaborolidin-5-one; and the like. of these, anhydrous aluminum chloride, anhydrous ferric chloride, zinc chloride, a borane-tetrahydrofuran complex, a borane-dimethyl sulfide complex, boron trichloride, boron tribromide, a boron trifluoride-diethyl ether complex, a chloroborane-diethyl ether complex, a chloroborane-dimethyl sulfide complex, a dichloroborane-dimethyl sulfide complex, a bromoborane-dimethyl sulfide complex, a dibromoborane-dimethyl sulfide complex and a boron compound such as the above-mentioned acyloxyborane compound, the above-mentioned dioxoborane compound or the above-mentioned oxazaborolidine compound is preferably used, and a boron compound is particularly preferably used in view of easiness of work-up and high selectivity of the obtained objective compound. The boron compound to be used in the present invention has Lewis acidity and the Lewis acidity refers to the property capable of accepting an unshared electron pair. The amount of the Lewis acid to be used is preferably 0.001 to 1 equivalent, more preferably 0.005 to 0.2 equivalent, relative to α,β-unsaturated carboxylic acid (I).

The amount of furan derivative (II) to be used is free of any particular limitation, but it is preferably 0.1 mole to 30 moles, more preferably 1 mole to 20 moles, per 1 mole of α,β-unsaturated carboxylic acid (I). In addition, the reaction temperature is preferably −80° C. to 80° C., more preferably −20° C. to 30° C. To preferentially obtain the endo form of a 7-oxabicyclo[2.2.1]hept-5-ene-2-carboxylic acid derivative, the reaction temperature is particularly preferably −10° C. to 5° C.

The reaction is preferably carried out by, for example, mixing α,β-unsaturated carboxylic acid (I), furan derivative (II) and, where necessary, a solvent, and then a Lewis acid to the resulting mixed solution, or mixing furan derivative (II), a Lewis acid and, where necessary, a solvent, and then α,β-unsaturated carboxylic acid (I) to the resulting mixed solution.

The 7-oxabicyclo[2.2.1]hept-5-ene-2-carboxylic acid derivative (III) or 7-oxabicyclo[2.2.1]hept-5-ene-2-carboxylic acid derivative (IV) thus obtained can be purified and separated according to a method generally employed for the purification and separation of organic compounds. For example, the reaction mixture is poured into water, extracted with an organic solvent such as pentane, hexane, petroleum ether, benzene, toluene, diethyl ether, diisopropyl ether, ethyl acetate, dichloromethane, chloroform and the like, and the extract is dried over anhydrous sodium sulfate and the like and concentrated. The obtained crude product is purified as necessary by recrystallization, distillation, chromatography and the like. Depending on the reaction conditions, a product is precipitated in the reaction mixture with the progress of the reaction, and the reaction mixture after the reaction may be filtered off as it is, or the reaction mixture may be cooled to allow precipitation of the product, and the resulting crystals may be isolated by filtration.

EXAMPLE

The present invention is described in more detail by means of the following Examples, which are not to be construed as limitative.

Example 1

The inside of a three-neck flask (inside volume 2000 ml) equipped with a thermometer and a mechanical stirrer was substituted with nitrogen, and distilled furan (816 g, 12 mol) and acrylic acid (288 g, 4.0 mol) were charged therein. The mixture was cooled to an inner temperature of 2° C. To this mixed solution was added dropwise a solution (43 ml, 0.04 mol) of a borane-tetrahydrofuran complex ($BH_3.THF$) in 0.93 M tetrahydrofuran over 20 min., while maintaining the inner temperature at not more than 2° C. After the completion of the dropwise addition, the mixture was stirred at the same temperature for 18 hr. The resulting crystals were collected by filtration through a glass filter, washed with hexane (300 ml) cooled to not more than 5° C. and dried under reduced pressure for 2 hr. to give endo-7-oxabicyclo[2.2.1]hept-5-ene-2-carboxylic acid as colorless crystals (352 g, purity >99%, yield 63% based on acrylic acid), that showed the following properties.

Endo-7-oxabicyclo[2.2.1]hept-5-ene-2-carboxylic Acid melting point: 90.0–91.0° C.; $^1$H-NMR spectrum (270 MHz, $CDCl_3$, TMS, ppm) δ: 1.55 (dd, 1H, J=10 Hz, 4 Hz), 2.13 (m, 1H), 3.17 (m, 1H), 5.06 (d, 1H, J=4 Hz), 5.23 (d, 1H, J=4 Hz), 6.28 (dd, 1H, J=6 Hz, 4 Hz), 6.45 (dd, 1H, J=6 Hz, 2 Hz)

Methanol (5 ml) was added to the mother liquor after filtration of the produced crystals and the mixture was concentrated to give 7-oxabicyclo[2.2.1]hept-5-ene-2-carboxylic acid (199 g, endo form:exo form=45:55, purity 90%, yield 32% based on acrylic acid). The $^1$H-NMR spectrum of the exo form were as follows.

Exo-7-oxabicyclo[2.2.1]hept-5-ene-2-carboxylic Acid $^1$H-NMR spectrum (270 MHz, $CDCl_3$, TMS, ppm) δ: 1.57 (dd, 1H, J=12 Hz, 8 Hz), 2.15 (m, 1H), 2.45 (dd, 1H, J=8 Hz, 4 Hz), 5.10 (d, 1H, J=4 Hz), 5.23 (s, 1H), 6.35 (m, 2H)

Example 2

The inside of a three-neck flask (inside volume 500 ml) equipped with a thermometer and a mechanical stirrer was substituted with nitrogen, and distilled furan (204 g, 3.0 mol) and acrylic acid (72 g, 1.0 mol) were charged therein. The mixture was cooled to an inner temperature of 2° C. To this mixed solution was added dropwise a borane-dimethyl sulfide complex ($BH_3$-$Me_2S$) (0.95 ml, 0.01 mol) over 2 min., while maintaining the inner temperature at not more than 2° C. After the completion of the dropwise addition, the mixture was stirred at the same temperature for 18 hr. The resulting crystals were collected by filtration through a glass filter, washed with hexane (100 ml) cooled to not more than 5° C. and dried under reduced pressure for 2 hr. to give 7-oxabicyclo[2.2.1]hept-5-ene-2-carboxylic acid as colorless crystals (81 g, endo form:exo form=92:8, purity >99%, yield 58% based on acrylic acid).

Example 3

The inside of a three-neck flask (inside volume 500 ml) equipped with a thermometer and a mechanical stirrer was substituted with nitrogen, and distilled furan (136 g, 2.0 mol), acrylic acid (72 g, 1.0 mol) and diisopropyl ether (70 ml) as a solvent were charged therein. The mixture was cooled to an inner temperature of 2° C. To this mixed solution was added dropwise a solution (11 ml, 0.01 mol) of a borane-tetrahydrofuran complex ($BH_3.THF$) in 0.93 M tetrahydrofuran over 10 min., while maintaining the inner temperature at not more than 2° C. After the completion of the dropwise addition, the mixture was stirred at the same temperature for 4 hr. The resulting crystals were collected by filtration through a glass filter, washed with diisopropyl ether (100 ml) cooled to not more than 5° C. and dried under reduced pressure for 2 hr. to give 7-oxabicyclo[2.2.1]hept-5-ene-2-carboxylic acid as colorless crystals (81 g, endo form:exo form=95:5, purity >99%, yield 58% based on acrylic acid).

Example 4

The inside of a three-neck flask (inside volume 100 ml) equipped with a thermometer and a mechanical stirrer was substituted with nitrogen, and distilled furan (41 g, 600 mmol) and acrylic acid (7.2 g, 100 mmol) were charged therein. The mixture was cooled to an inner temperature of 2° C. To this mixed solution was added dropwise a boron trifluoride-diethyl ether complex ($BF_3.(C_2H_5)_2O$) (0.1 ml, 1.0 mmol) over 1 min., while maintaining the inner temperature at not more than 2° C. After the completion of the dropwise addition, the mixture was stirred at the same temperature for 5 hr. Water (10 ml) was added to the reaction mixture and the organic layer and the aqueous layer were separated. The aqueous layer was extracted twice with dichloromethane (10 ml) and the extract was combined with the organic layer separated earlier. The mixture was dried over anhydrous sodium sulfate, concentrated and dried under reduced pressure for 2 hr. to give 7-oxabicyclo[2.2.1]hept-5-ene-2-carboxylic acid as colorless crystals (6.0 g, endo form:exo form =69:31, purity 96% (containing 4% of unreacted acrylic acid), yield 41% based on acrylic acid).

Example 5

Distilled furan (20.4 g, 300 mmol) and acrylic acid (7.2 g, 100.0 mmol) were charged in a similar reactor as in Example 4, and the mixture was cooled to an inner temperature of 2° C. To this mixed solution was added dropwise a solution (1.1 ml, 1.0 mmol) of a borane-tetrahydrofuran complex ($BH_3.THF$) in 0.93 M tetrahydrofuran over 5 min., while maintaining the inner temperature at not more than 2° C. After the completion of the dropwise addition, the mixture was stirred at the same temperature for 25 hr. Water (10 ml) and chloroform (10 ml) were added to the reaction mixture and the organic layer and the aqueous layer were separated. The aqueous layer was extracted twice with chloroform (10 ml) and the extract was combined with the organic layer separated earlier. The mixture was dried over anhydrous sodium sulfate, concentrated and dried under reduced pressure for 2 hr. to give 7-oxabicyclo[2.2.1]hept-5-ene-2-carboxylic acid as pale yellow crystals (12.6 g, endo form:exo form=77:23, purity 97% (containing 3% of unreacted acrylic acid), yield 87% based on acrylic acid).

Example 6

3-Methylfuran (15.4 g, 187 mmol) and acrylic acid (7.2 g, 100 mmol) were charged in a similar reactor as in Example 4, and the mixture was cooled to an inner temperature of 2° C. To this mixed solution was added dropwise a solution (1.1 ml, 1.0 mmol) of a borane-tetrahydrofuran complex ($BH_3.THF$) in 0.93 M tetrahydrofuran over 5 min., while maintaining the inner temperature at not more than 2° C. After the completion of the dropwise addition, the mixture was stirred at the same temperature for 24 hr. The resulting crystals were collected by filtration through a glass filter, washed with hexane (10 ml) cooled to not more than 5° C. and dried under reduced pressure for 2 hr. to give endo-6-methyl-7-oxabicyclo[2.2.1]hept-5-ene-2-carboxylic acid as colorless crystals (1.9 g, purity >99%, yield 9.5% based on acrylic acid), which showed the following properties.

Endo-6-methyl-7-oxabicyclo[2.2.1]hept-5-ene-2-carboxylic Acid melting point: 129.5 to 130.0° C.; $^1$H-NMR spectrum (270 MHz, $CDCl_3$, TMS, ppm) δ: 1.56 (dd, 1H, J=12 Hz, 4 Hz), 1.86 (d, 3H, J=2 Hz), 2.08 (m, 1H), 3.18 (m, 1H), 4.76 (d, 1H, J=5 Hz), 5.10 (d, 1H, J=4 Hz), 5.82 (d, 1H, J=2 Hz)

Example 7

The inside of a three-neck flask (inside volume 25 ml) equipped with a thermometer and a magnetic stirrer was substituted with nitrogen, and distilled furan (4.1 g, 60 mmol) and acrylic acid (3.6 g, 50.0 mmol) were charged therein. Then, zinc chloride (0.68 g, 5.0 mmol) was added and the mixture was stirred at 20° C. for 21 hr. Water (10 ml) and chloroform (10 ml) were added to the reaction mixture and the organic layer and the aqueous layer were separated. The aqueous layer was extracted twice with chloroform (10 ml) and the extract was combined with the organic layer separated earlier. The mixture was dried over anhydrous sodium sulfate, concentrated and dried under reduced pressure for 2 hr. to give 7-oxabicyclo[2.2.1]hept-5-ene-2-carboxylic acid as pale yellow crystals (3.8 g, endo form:exo form=64:36, purity 95% (containing 5% of unreacted acrylic acid), yield 51% based on acrylic acid).

Example 8

Distilled furan (17.0 g, 250 mmol) and maleic acid (5.8 g, 50.0 mmol) were charged in a similar reactor as in Example 4, and the mixture was cooled to an inner temperature of 2° C. To this mixed solution was added dropwise a solution (5.4 ml, 5.0 mmol) of a borane-tetrahydrofuran complex ($BH_3.THF$) in 0.93 M tetrahydrofuran over 20 min., while maintaining the inner temperature at not more than 2° C. After the completion of the dropwise addition, the mixture was stirred at the same temperature for 5 hr. The resulting crystals were collected by filtration through a glass filter, washed with hexane (30 ml) cooled to not more than 5° C. and dried under reduced pressure for 2 hr. to give endo, endo-7-oxabicyclo[2.2.1]hept-5-ene-2,3-dicarboxylic acid as colorless crystals (4.1 g, purity >99%, yield 45% based on maleic acid), which showed the following properties.

Endo,endo-7-oxabicyclo[2.2.1]hept-5-ene-2,3-dicarboxylic Acid melting point: 148.0 to 149.0° C. $^1$H-NMR spectrum (270 MHz, DMSO-$d_6$, TMS, ppm) δ: 3.25 (s, 2H), 5.01 (s, 2H), 6.24 (s, 2H).

Example 9

Distilled furan (6.8 g, 100 mmol) and 2-bromoacrylic acid (1.0 g, 6.6 mmol) were charged in a similar reactor as in Example 7, and the mixture was cooled to an inner temperature of 2° C. To this mixed solution was added dropwise a solution (0.7 ml, 0.7 mmol) of a borane-tetrahydrofuran complex ($BH_3.THF$) in 0.93 M tetrahydrofuran over 5 min., while maintaining the inner temperature at not more than 2° C. After the completion of the dropwise addition, the mixture was stirred at the same temperature for 10 hr. Water (10 ml) and chloroform (10 ml) were added to the reaction mixture and the organic layer and the aqueous layer were separated. The aqueous layer was extracted twice with chloroform (10 ml) and the extract was combined with the organic layer separated earlier. The mixture was dried over anhydrous sodium sulfate, concentrated and dried under reduced pressure for 2 hr. to give 2-bromo-7-oxabicyclo[2.2.1]hept-5-ene-2-carboxylic acid as a pale-yellow oily substance (1.3 g, main component:minor component=2:1, purity 77% (containing 23% of unreacted 2-bromoacrylic acid), yield 70% based on 2-bromoacrylic acid) being a mixture of an endo form and an exo form.

Main Component $^1$H-NMR spectrum (270 MHz, CDCl$_3$, TMS, ppm) δ: 1.74 (d, 1H, J=13 Hz), 2.94 (dd, 1H, J=13 Hz, 5 Hz), 5.10 (dd, 1H, J=5 Hz, 2 Hz), 5.47 (s, 1H), 6.40 (dd, 1H, J=7 Hz, 2 Hz), 6.59 (d, 1H, J=7 Hz)

Minor Component $^1$H-NMR spectrum (270 MHz, CDCl$_3$, TMS, ppm) δ: 2.41 (d, 1H, J=13 Hz), 2.57 (dd, 1H, J=13 Hz, 5 Hz), 5.15 (dd, 1H, J=5 Hz, 2 Hz), 5.21 (s, 1H), 6.50 (dd, 1H, J=7 Hz, 2 Hz), 6.59 (d, 1H, J=7 Hz)

Example 10

Distilled furan (9.4 g, 138 mmol) and acrylic acid (1.8 g, 25.0 mmol) were charged in a similar reactor as in Example 7, and then anhydrous ferric chloride (0.41 g, 2.5 mmol) was added. The mixture was stirred under a nitrogen atmosphere at an inner temperature of 5° C. for 5 hr. Water (10 ml) and chloroform (10 ml) were added to the reaction mixture and the organic layer and the aqueous layer were separated. The aqueous layer was extracted twice with chloroform (10 ml) and the extract was combined with the organic layer separated earlier. The mixture was dried over anhydrous sodium sulfate, concentrated and dried under reduced pressure for 2 hr. to give 7-oxabicyclo[2.2.1]hept-5-ene-2-carboxylic acid as pale-yellow crystals (3.1 g, endo form:exo form=64:36, purity 94% (containing 6% of unreacted acrylic acid), yield 83% based on acrylic acid).

Example 11

Distilled furan (9.4 g, 138 mmol) and acrylic acid (1.8 g, 25.0 mmol) were charged in a similar reactor as in Example 7, and then anhydrous aluminum chloride (0.33 g, 2.5 mmol) was added. The mixture was stirred under a nitrogen atmosphere at an inner temperature of 5° C. for 5 hr. Water (10 ml) and chloroform (10 ml) were added to the reaction mixture and the organic layer and the aqueous layer were separated. The aqueous layer was extracted twice with chloroform (10 ml) and the extract was combined with the organic layer separated earlier. The mixture was dried over anhydrous sodium sulfate, concentrated and dried under reduced pressure for 2 hr. to give 7-oxabicyclo[2.2.1]hept-5-ene-2-carboxylic acid as pale-yellow crystals (3.0 g, endo form:exo form=67:33, purity 93% (containing 7% of unreacted acrylic acid), yield 80% based on 5 acrylic acid).

Example 12

Distilled furan (141.7 g, 2.08 mol) and triacetoxyborane (1.19 g, 6.63 mmol) were charged in a similar reactor as in Example 4, and the mixture was cooled to −5° C. To this mixed solution was added acrylic acid (30.4 g, 0.42 mol) and the mixture was stirred at an inner temperature of −5° C. for 22 hr. The resulting crystals were collected by filtration through a glass filter, washed with diisopropyl ether (60 ml) cooled to not more than 5° C. and dried under reduced pressure for 2 hr. to give 7-oxabicyclo[2.2.1]hept-5-ene-2-carboxylic acid as colorless crystals (11.4 g, endo form:exo form=98:2, purity >99%, yield 43% based on acrylic acid).

Example 13

Distilled furan (141.7 g, 2.08 mol) and tripropionyloxyborane (1.55 g, 6.75 mmol) were charged in a similar reactor as in Example 4, and the mixture was cooled to −5° C. To this mixed solution was added acrylic acid (30.1 g, 0.42 mol) and the mixture was stirred at an inner temperature of −5° C. for 15 hr. The resulting crystals were collected by filtration through a glass filter, washed with diisopropyl ether (60 ml) cooled to not more than 5° C. and dried under reduced pressure for 2 hr. to give 7-oxabicyclo[2.2.1]hept-5-ene-2-carboxylic acid as colorless crystals (22.5 g, endo form:exo form=99:1, purity>99%, yield 39% based on acrylic acid).

Industrial Applicability

According to the present invention, 7-oxabicyclo[2.2.1]hept-5-ene-2-carboxylic acid derivatives, particularly an endo form thereof, can be industrially advantageously produced directly from α,β-unsaturated carboxylic acid (I) and furan derivative (II) under mild conditions in a high yield. The method of the present invention can advantageously produce 7-oxabicyclo[2.2.1]hept-5-ene-2-carboxylic acid derivatives, particularly an endo form thereof, under mild conditions (i.e., without heating at a high temperature or pressurization) in a shorter reaction time in a high yield, as compared to conventional methods, and is suitable for industrial production.

This application is based on a patent application No. 2000-282140 filed in Japan, the contents of which are hereby incorporated by reference.

What is claimed is:

1. A production method of a 7-oxabicyclo[2.2.1]hept-5-ene-2-carboxylic acid derivative of the formula (III)

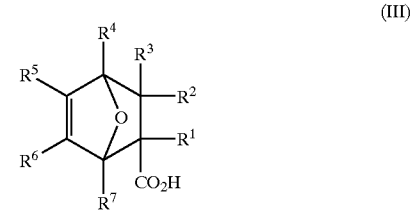

(III)

wherein $R^1$, $R^2$ and $R^3$ are each independently a hydrogen atom, a halogen atom, a formyl group, a cyano group, a carboxyl group, an alkoxycarbonyl group, an acyl group, an acyloxy group, an organic sulfinyl group, an organic sulfonyl group or an alkyl group optionally having substituents, or $R^1$ and $R^2$ may form a ring together with the carbon atoms they are bonded to; and $R^4$, $R^5$, $R^6$ and $R^7$ are independently a hydrogen atom, an alkoxyl group, an alkylthio group or an alkyl group optionally having substituents, or $R^4$ and $R^5$, and $R^5$ and $R^6$ may form a ring together with the carbon atoms they are bonded to, or the formula (IV)

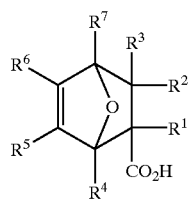

(IV)

wherein $R^1$, $R^2$, $R^3$, $R^4$, $R^5$, $R^6$ and $R^7$ are as defined above, which comprises:

reacting an α,β-unsaturated carboxylic acid of the formula (I)

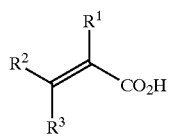

(I)

wherein $R^1$, $R^2$ and $R^3$ are as defined above, with a furan derivative of the formula (II)

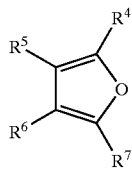

(II)

wherein $R^4$, $R^5$, $R^6$ and $R^7$ are as defined above, in the presence of a Lewis acid.

2. A production method of a 7-oxabicyclo[2.2.1]hept-5-ene-2-carboxylic acid derivative of the formula (III-1)

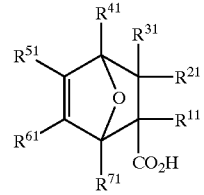

(III-1)

wherein $R^{11}$, $R^{21}$ and $R^{31}$ are each independently a hydrogen atom, a halogen atom or a carboxyl group, or $R^{11}$ and $R^{21}$ may form a ring together with the carbon atoms they are bonded to, and $R^{41}$, $R^{51}$, $R^{61}$ and $R^{71}$ are each independently a hydrogen atom or an alkyl group optionally having substituents, or $R^{41}$ and $R^{51}$, and $R^{51}$ and $R^{61}$ may form a ring together with the carbon atoms they are bonded to, or the formula (IV-1)

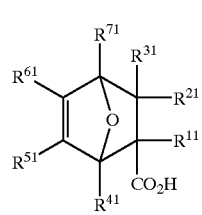

(IV-1)

wherein $R^{11}$, $R^{21}$, $R^{31}$, $R^{41}$, $R^{51}$, $R^{61}$ and $R^{71}$ are as defined above, which comprises:

reacting an α,β-unsaturated carboxylic acid of the formula (I-1)

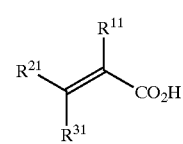

(I-1)

wherein $R^{11}$, $R^{21}$ and $R^{31}$ are as defined above, with a furan derivative of the formula (II-1)

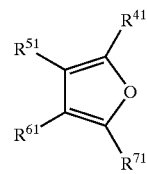

(II-1)

wherein $R^{41}$, $R^{51}$, $R^{61}$ and $R^{71}$ are as defined above, in the presence of a Lewis acid.

3. The production method of claim 1 or 2, wherein a boron compound having Lewis acidity is used as the Lewis acid.

4. The production method of claim 1 or 2, wherein the Lewis acid is selected from the group consisting of a borane-tetrahydrofuran complex, a borane-dimethyl sulfide complex, a boron trifluoride-diethyl ether complex, triacetoxyborane and tripropionyloxyborane.

* * * * *